United States Patent [19]
Kawashima et al.

[11] 3,962,038
[45] June 8, 1976

[54] PREPARATION OF WATER-INSOLUBLE ENZYMES

[75] Inventors: Koji Kawashima, Chofu; Keiji Umeda, Tokyo, both of Japan

[73] Assignee: Director of National Food Research Institute, Japan

[22] Filed: Apr. 10, 1974

[21] Appl. No.: 459,624

Related U.S. Application Data

[63] Continuation-in-part of Ser. No. 332,239, Feb. 14, 1973, abandoned.

[30] Foreign Application Priority Data

Mar. 9, 1972 Japan................................ 47-24150

[52] U.S. Cl.................................. 195/68; 195/63; 195/DIG. 11; 204/159.16; 204/159.22
[51] Int. Cl.²........................................... C07G 7/02
[58] Field of Search................ 195/63, 68, DIG. 11; 204/154, 159.22, 159.16, 159.15

[56] References Cited
UNITED STATES PATENTS

| | | | |
|---|---|---|---|
| 3,081,244 | 3/1963 | Campanile........................... | 204/154 |
| 3,137,643 | 6/1964 | Bell et al............................. | 204/154 |
| 3,770,588 | 11/1973 | Forgione............................. | 195/68 X |

FOREIGN PATENTS OR APPLICATIONS

| | | |
|---|---|---|
| 1,955,638 | 6/1970 | Germany |

OTHER PUBLICATIONS

Hicks, et al., The Preparation and Characterization of Lyophilized Polyacrylamide Enzyme Gels for Chemical Analysis, Analytical Chemistry, vol. 38, No. 6, 1966 (pp. 726–730).

*Primary Examiner*—David M. Naff
*Attorney, Agent, or Firm*—McGlew and Tuttle

[57] ABSTRACT

Water-insoluble enzymes are prepared by mixing an enzyme with at least one water soluble monomer selected from the group consisting of acrylamide, bisacrylamide, acrylic acid, sodium acrylate, potassium acrylate and calcium acrylate, freezing the resulting mixture at a temperature below about $-5°C$ and irradiating the frozen mixture with gamma rays or x-rays under aerobic conditions to polymerize said monomer and entrap the enzyme in the resulting polymer material. The frozen irradiated polymer material can be thawed at room temperature or can be lyophilized to produce a spongelike, membrane form that maintains its structure when immersed in water. Before freezing the enzyme and monomer mixture, an organic substance can be incorporated which promotes polymerization yield and protects the enzyme from radiation inactivation.

10 Claims, No Drawings

PREPARATION OF WATER-INSOLUBLE ENZYMES

CROSS REFERENCE TO OTHER APPLICATION

This application is a continuation-in-part of my co-copending application Ser. No. 332,239 filed Feb. 14, 1973, now abandoned.

BACKGROUND AND SUMMARY OF THE INVENTION

1. Prior Art

Generally, enzyme proteins are water soluble and enzyme reactions are usually carried out in the solubilized state. Enzyme reactions cannot be done continuously on an industrial scale due to above mentioned properties of enzymes. Also, separation and purification of the reaction product cannot be conducted effectively.

Therefore, to resolve these problems many attempts have been made for insolubilizing enzymes. Methods which have been developed so far can be divided into four groups, i.e. adsorption method, carrier binding method, crosslinking method and entrapping method.

However, these prior art methods have disadvantages:

(1) Adsorption or binding of enzyme to carrier is not always efficient. Consequently, the enzyme leaks frequently. (2) Enzyme activity is low and unstable. (3) Manufacturing process is tedious. (4) They can be applied only to a highly purified enzyme.

When the radiopolymerization of water soluble monomers such as acrylamide is conducted, oxygen was known to inhibit the radial polymerization, therefore until now when radiopolymerization is carried out the solution to be polymerized is usually bubbled with Nitrogen or Argon. Thus, from the solution and its surroundings, oxygen is completely expelled, and then finally radio-polymerization is conducted.

According to the above-mentioned prior art method, namely under anaerobic and unfrozen conditions, radio-polymerization was conducted. According to the present invention, however, it is necessary to expel oxygen from the solution and its surroundings, thus making the process very simple and having a great advantage over the prior art process.

Because of the difference in the new method of the present invention and the old method of the prior art, the final product obtained also is very different. When radio polymerization is conducted without freezing (as in the prior art), the polymer is obtained as a curdy precipitate, but according to the method of the present invention the solution is polymerized as a whole, like spongy mass. This gives a product of more uniform consistency.

The very substantial difference between the present invention and the process disclosed in the prior art has been explained hereinabove. Further, according to the present invention, radio polymerization as shown in the examples of the specification was conducted under aerobic conditions at the frozen state and thus this process of the present invention is very useful.

2. Summary of the Invention

The present invention relates to a method for producing water-insoluble enzymes so as to obtain water-insoluble enzymes having high activity and stability by a simple method. That is to say, our invention comprises freezing a solution of one or more monomers and enzyme, and then polymerizing the resultant composition by irradiating same with a dose of about 40 – 100 Krad of gamma ray. This method entraps the active enzyme within the resulted polymer lattice. Before freezing the solution an organic substance can be incorporated which promotes the polymerization yield and protects the highly purified enzyme from radiation inactivation. Further, our invention includes a new improved technique of drying under vacuum (lyophilization) immediately after irradiating the frozen solution.

DESCRIPTION OF THE INVENTION

Firstly, a solution containing one or more water soluble monomers and enzyme, and if necessary with an organic substance, is frozen and then irradiated. Then immediately after irradiating, the frozen solution is thawed at room temperature, and if necessary, the frozen solution can be dried under vacuum (lyophilization) and by this technique better results are obtained.

There are several advantages in radiation entrapping of enzymes according to our invention, in contrast with chemical ones, such as:

1. Water soluble monomers which polymerize with ionizing radiation are applicable even if they do not chemically polymerize;
2. There is no enzyme inactivation due to chemical catalyzer;
3. Polymerization is conducted at the frozen temperature;
4. Beginning or stopping of polymerization is controlled freely.

The following water soluble monomers are used in practicing the present invention: acrylic acid, acrylamide, bisacrylamide (N,N'-methylene bisacrylamide), sodium acrylate, potassium acrylate, acrylonitrile, acrylic acid esters and other acrylic acid derivatives, propylene glycol. Also, it should be understood that other water soluble monomers can also be used in practicing the present invention.

The following enzymes can be applied usefully in practicing this invention: amylase, protease, glucoamylase, lipase, acrylase, d-amino acid oxidase, catalase, various kinds of dehydrogenase, urease, ribonuclease, and the like.

The enzymes listed above are illustrative and not be considered restrictive. In the present invention, enzymes which are not purified sufficiently can be used and even a micro-organism itself can be usefully applied in the process of the invention. Multi insolubilized enzymes can be produced by the method of the present invention.

Certain organic substance means a substance which promotes the polymerization yield of monomer and which at the same time protects enzymes, especially highly purified enzymes in the solution from radiation inactivation. The existence of the said substance is very important in the radiation polymerization of acrylamide and bisacrylamide. Examples of the said organic substance are: substrate of the enzyme, starch, glycerine, sugar such as glucose, and protein such as defatted powdered milk.

Examples of suitable ionizing radiation are the gamma ray ($^{60}$Co, $^{137}$Cs), X-ray, accelerated electron ray and the like.

In this invention, the freezing treatment is conducted below −5°C and preferable temperatures would be −20°C to −100°C. The solution is placed in a suitable container like a flask or beaker and placed in a coolant, without bubbling nitrogen or argon, which completes the freezing technique. When the quantity is large, a thick frozen layer is obtained and when the quantity is small, the layer obtained is thin. For the purpose of obtaining a thinner layer, the container with the solution is slowly rotated inside the coolant and after this when the frozen layer is irradiated by ionizing radiation, a membranous, water-insoluble polymer is obtained. As regards the coolant, a liquid coolant is preferred because of its easy heat conductivity.

We used the generally known dry ice-acetone ($-86°C$) for freezing but any other ordinarily used coolant could also be used. Dry ice-acetone was used because constant temperatures could be easily and quickly maintained, and at such low temperatures freezing is very quick.

When the solution is frozen, the water in it forms small ice crystals and the monomer, enzyme and organic substance becomes encircled around these ice crystals. When these ice crystals are exposed to an ionizing radiation of from about 40 to about 100 Krad, the enzyme becomes distributed in the resultant polymer. During the irradiation process, the frozen mixture is placed in the coolant.

The resultant membraneous water-insoluble polymer, by defreezing at room temperature, assumes a hollow appearance where ice crystals were present and assumes a sponge-like mass, which maintains its structure even on immersing in water.

Irradiation was carried out under aerobic conditions with gamma ray or X-ray. The critical dose for irradiation is from about 40 to about 100 Krad, if the dose is less than about 40 Krad, there is inadequate polymerization and if doses higher than about 100 Krad are used, the enzyme is bound to get inactivated. Immediately after irradiation, if desired, drying under vacuum (lyophilization) is conducted and the activity (comparing with the total activity of the original enzyme) of the immobilized enzyme is increased. Lyophilization is carried out in the normal way.

Water-insoluble enzyme prepared by the method of this invention is a whitish membrane. This membrane, if necessary, if finely cut or powdered. The preparation obtained through the lyophilization step can be powdered easily without any significant drop in enzyme activity.

The activity of the enzyme is very stable and is scarcely decreased after several applications.

There are many methods to immobilize enzymes. Among them, the so-called entrap method is characterized by its simplicity and versatility. But immobilized enzymes in this method are surrounded by polymer and the contact of enzyme with its substrate is rather limited. To resolve this problem, attempts have been made to apply carriers with large surface area such as polyurethane foam, cottom wool, filter paper and so on.

In the method of this invention, no carrier is necessary, and the immobilized enzyme preparation itself is processed to have a sponge-like appearance with large surface area which will not loose its structure even in water.

The present invention is further illustrated in the following examples, which are not to be considered to limit the invention.

EXAMPLE 1

To 2 ml of a solution of 30 g of acrylamide and 1.6 g of bis-acrylamide in 100 ml of 1/25M acetate buffer at pH 4.6 were added with 2.0 ml of 10% soluble starch and 1.0 ml of invertase solution (0.25 mg invertase/ml of the buffer).

This mixture is placed in a 300 ml round bottom flask and immersed in the coolant (dry ice-acetone). The flask is slowly rotated while the flask is inside the coolant so as to obtain a thin layer on the wall of the flask.

After thus freezing, while maintaining the frozen state, the mixture was irradiated with 42.8 Krad by $^{60}Co$. This irradiated mixture is defrozen at room temperature to obtain a water-insoluble enzyme preparation.

One fiftieth of the above enzyme preparation, 5 ml of 0.3M sucrose and 4 ml of 1/25M acetate buffer at pH 4.6 were mixed and incubated at 40°C for 60 min.

After termination of reaction, the enzyme activity was assayed by the modified Somogy method. The reocvery of enzyme activity of the preparation was found to be 69.2% based on original activity.

EXAMPLE 2

To 2 ml of a solution of 30 g of acrylamide and 1.6 g of bis-acrylamide in 100 ml of tris-glycerol buffer at pH 7.0 were added 2 ml of 1% soluble starch dissolved in the buffer and 1 ml of glucose-oxidase solution (0.5 mg enzyme/ml of the buffer).

The mixture was frozen as in Example 1 and was treated with 50.4 Krad by $^{60}Co$. This preparation was found to have 25.3% recovery of enzymic activity based on starting enzyme.

EXAMPLE 3

Two ml of a solution composed of 30 g of acrylamide, 1.6 g of bis-acrylamide, 100 ml of 1/20M borate buffer, pH 8.3 and 10 g of soluble starch was mixed with 0.5 ml of D-amino acid oxidase solution (50 mg/ml) and was frozen, then followed by treatment with 49.9 Krad by $^{60}Co$ to give a whitish water-insoluble enzyme preparation.

The enzyme activity of this preparation was assayed as follows: 5 ml of borate buffer (pH 8.3, 1/20M), 1 ml of dl- alanine (100 mM/ml), 1 ml of catalase (3 mg/25 ml) and 1/50th of insolubilized enzyme were mixed and incubated at 30°C for 60 minutes. Resultant pyruvic acid was determined by colorimetric method.

The recovery of enzymic activity of the preparation was found to be 25.0%.

EXAMPLE 4

Two ml of a solution at pH 8.0 containing 30 g of acrylamide, 1.6 g of bis-acrylamide and 100 ml of water, 2 ml of 10% soluble starch and 1 ml of 2% acylase solution were mixed together and frozen.

By irradiation treatment of $^{60}Co$ (53.5 Krad), a water-insoluble enzyme preparation was obtained.

1/10M Beronal buffer, pH 8.0 (6 ml), $1/2 \times 10^{-3}M$ $CoCl_2$ (2 ml), the preparation washed thoroughly with water (1 g) and substrate (2 ml) (1/10M N-acetyl dl-methionine) were mixed and incubated at 37°C for 30 minutes. Three ml aliquots of the reaction mixture was taken out and boiled for 3 minutes. To it were added 2 ml of ninhydrin solution and 0.1 ml of 1/100M $SnCl_2$. The mixture was boiled for 20 minutes. After cooling, 10 ml of 50% n-propyl alcohol was added and its appeared color was determined at 570 mμ.

As a control, 1 ml of a soluble acylase solution was employed and assayed as mentioned above.

The enzyme activity of the water-insoluble enzymes was 39.2% compared to soluble one.

EXAMPLE 5

To 2 ml of a solution containing 30 g of acrylamide and 0.8 g of bis-acrylamide in 100 g of water were added 1 ml of 50% D-glucose solution, 0.5 ml of 2/5M phosphate buffer (pH 7.5) and 1.5 ml of a 5% suspension of freeze-dried D-glucose isomerase production microorganism (1/20M, pH 7.5 phosphate buffer). The mixture was frozen and then, subjected to 50.5 Krad of irradiation. The recovery of enzymic activity of the obtained water-insoluble preparation was 25.1%.

Besides, when, instead of the suspension of glucose isomerase producing microorganism, 1.5 ml of a crude enzyme solution (18.5 mg/ml, 1/20M phosphate buffer at pH 7.5) which was obtained by sonic treatment, salting out and dialysis of the said microorganism, was used, the reocvery of enzyme activity of the preparation thus obtained was 42.2%.

EXAMPLE 6

To 2 ml of a solution containing 30 g of acrylamide, 1.6 g of bis-acrylamide and 100 g of water, were added with 1.5 ml of 5% pancreatine solution (1/20M phosphate buffer, pH 8.0), 0.5 ml of 2/5M phosphate buffer at pH 8.0 and 1 ml of 50% D-glucose solution. The mixture was frozen as in Example 1 and then, subjected to 52 Krad of an ionizing radiation ($^{60}$Co).

The water-insoluble polymer thus obtained was finely divided and incubated with 1.5% casein solution as a substrate. The enzyme activity was determined by the Anson method. The recovery of the enzyme activity in this preparation was 10.5%.

When the freezing step was omitted, the activity of the resultant enzyme preparation was 4.1%.

EXAMPLE 7

To 2 ml of a solution containing 45 g of acrylamide and 2 g of bis-acrylamide in 100 g of water, were added 1 ml of 1% Mould amylase solution (commercial name: Biozyme A, pH 5.6, 1/50M phosphate buffer) and 2 ml of 1/50M citrate buffer (pH 5.6) (or 2 ml of 5% soluble starch dissolved in the buffer).

The mixture was frozen as in Example 1 and then, subjected to 47 Krad of an ionizing radiation ($^{60}$Co). The resultant product is water-insoluble. The product was thoroughly washed with water after dividing it finely.

The activity of this preparation was assayed on 20 min. incubation at 30°C by using 5% soluble starch as a substrate, followed by measurement of the produced reducing sugar using 2,4-dinitrosalicylic acid method. The recovery of the enzyme activity of the preparation was 12.2%. When the freezing step was omitted, the enzyme activity was 5.4%.

EXAMPLE 8

To 2 ml of a solution containing 50 g of acrylamide, 2 g of bis-acrylamide and 100 g water, were added 1 ml of 1% Takadiastase solution (pH 5.6, 1/50M citrate buffer) and 2 ml of 5% soluble starch solution (pH 5.6, 1/50M citrate buffer). The resultant mixture was frozen and then, irradiated with 60.2 Krad by $^{60}$Co to polymerize the mixture. The resultant product was thoroughly washed after dividing it finely, and 1/25th of it then incubated at 30°C for 20 minutes in the presence of 10 ml of 5% soluble starch as a substrate.

The resultant reducing sugar was determined by the dinitrosalicylic method. The recovery of enzyme activity of the preparation thus obtained was 7.9% based on the original activity.

EXAMPLE 9

To 2 ml of a solution of 30 g of acrylamide and 1.6 g of bis-acrylamide in 100 ml of tris-glycerol buffer (pH 7.0) were added 2 ml of 10% soluble starch in the buffer and 1 ml of glucose oxidase solution (0.5 mg/ml of the buffer).

The mixture was frozen and was subjected to 50.4 Krad of irradiation followed by freeze-drying. A water-insoluble enzyme preparation obtained was washed fully with water.

One fiftieth of the preparation was added to a reaction mixture of 1 ml of glucose solution (50 mg/ml), 1 ml of o-dianisidine (2 mg/10 ml ethyl alcohol) and 1 ml of peroxidase (60 α/ml) and the mixture was incubated at 37°C for 60 minutes. By addition of 4 ml of 5N-HCl the reaction was terminated and also the color was developed.

Enzymatic activity of the preparation was determined colorimetrically at 525 mμ. The recovery of the activity was 33.7%.

EXAMPLE 10

To 2.0 ml of a solution of 30 g of acrylamide, 1.6 g of bis-acrylamide, 100 ml of 1/20M borate buffer at pH 8.3 and 10 g of soluble starch was added 0.5 ml of D-amino acid oxidase solution (60 mg/ml). The mixture was frozen and then, irradiated with 49.9 Krad of $^{60}$Co irradiation followed by lyophilization.

Enzyme activity of the preparation obtained was assayed colorimetrically at 505 mμ by measuring the amount of pyruvic acid produced. The recovery of the activity was 66.7%. Also, the activity of the preparation after 5 times uses was 67.8% and the average activity was 65.5%.

EXAMPLE 11

To 2 ml of a solution of 30 g of acrylamide, 1.6 g of bis-acrylamide and 100 g of water were added 2 ml of 10% soluble starch solution and 1 ml of 2% acylase solution. The mixture was frozen and was subjected to 55.2 Krad of $^{60}$Co irradiation followed by lyophilization.

The thus obtained water-insoluble membraneous substance was washed thoroughly with water. The enzyme activity was determined by the following method; i.e. the reaction mixture of 6 ml of 1/10M Beronal buffer at pH 8.0, 2 ml of 1/2 × 10$^{-3}$M CoCl$_2$, 1 g of a washed immobilized enzyme and 2 ml of substrate (1/10M, N-acetyl-D,L-methionine) was incubated at 37°C for 30 minutes. After termination of the reaction, 2 ml of the reaction mixture was boiled and was added 2 ml of ninhydrin solution and 0.1 ml of 1/100M SnCl$_2$. The mixture was further boiled for 20 minutes. After cooling, the mixture was added with 10 ml of 50% propyl alcohol. The activity was assayed by colorimetry at 570 mμ. The recovery of the activity was 45.5%.

EXAMPLE 12

Solutions A, B and C were prepared respectively, and their composition is as follows:

Solution A: 30% sodium acrylate solution
Solution B: 30 g of acrylamide, 1.6 g of bis-acrylamide, and 100 ml of water
Solution C: 1% amylase solution.

These solutions were mixed together in the range described in Table 1 and thus, samples 1, 2, 3, and 4 were prepared.

Table 1

| Sample | Solution A | B | C |
|---|---|---|---|
| | ml | ml | ml |
| 1 | 0 | 4.0 | 1.0 |
| 2 | 1.2 | 2.8 | 1.0 |
| 3 | 2.0 | 2.0 | 1.0 |
| 4 | 2.4 | 1.6 | 1.0 |

Samples 1, 2, 3 and 4 were frozen respectively. These samples were subjected to 52.4 Krad of $^{60}$Co irradiation and then, were lyophilized. The so-obtained water-insoluble membraneous material was washed thoroughly with buffer solution. The material in 1/25M citrate buffer at pH 5.6 was added with substrate (1% soluble starch) and was incubated at 30°C for 10 minutes. After termination of the reaction, the resulting reducing sugar content was estimated by the Somogy method using 6 ml of the reaction mixture.

The recovery of the activity was shown in Table 2.

Table 2

| Sample | Activity |
|---|---|
| 1 | 17.8% |
| 2 | 30.0 |
| 3 | 61.1 |
| 4 | 55.6 |

EXAMPLE 13

In this example, insolubilization of three types of protease, i.e. alkaline protease (pH 10.0), neutral protease (pH 8.0) and acidic protease (pH 3.0) was carried out.

Solutions A, B and C were prepared respectively, and their composition is as follows:

Solution A: 30 g of acrylamide, 1.6 g of bis-acrylamide, 100 ml of buffer solution
Solution B: 30% sodium acrylate solution
Solution C: 0.2% protease solution.

These solutions were mixed together in the range described in Table 3 and samples 1, 2 and 3 were prepared.

Table 3

| Sample | Solution A | B | C |
|---|---|---|---|
| | ml | ml | ml |
| 1 | 2.4 | 1.6 | 1.0 |
| 2 | 2.0 | 2.0 | 1.0 |
| 3 | 4.0 | 0 | 1.0 |

Samples 1, 2 and 3 were frozen respectively. Samples 1 and 2 were irradiated with 52.5 Krad by $^{60}$Co and Sample 3 was irradiated with 73 Krad by $^{60}$Co.

Each of the insoluble enzyme preparation obtained was added to a buffer solution. The solution was mixed with 1% casein solution and was incubated at 37°C for 15 minutes. 2 ml of the reaction mixture was added to 2 ml of 0.4M trichloracetic acid and the mixture was filtered. 0.4M sodium carbonate and Folin reagent were added to the filtrate to develop the color.

The enzyme activity was assayed by measuring colorimetrically at 660 m$\mu$.

In this example, buffer solutions used were as follows:
borate-sodium carbonate buffer at pH 10.0 for alkaline protease;
Phosphate buffer at pH 8.0 for neutral protease;
hydrochloric acid-sodium acetate buffer at pH 3.0 for acidic protease.

Protease activity of the preparations determined by the Folin method was shown in Table 4.

Table 4

| Enzyme \ Sample | 1 | 2 | 3 |
|---|---|---|---|
| alkaline protease (pH 10.0) | 10.6% | 10.6% | 1.6% |
| neutral protease (pH 8.0) | 13.3 | 16.9 | 8.3 |
| acidic protease (pH 3.0) | 27.6 | 37.9 | 3.5 |

The change of the activity when the preparations were used repeatedly was shown in Table 5. It was confirmed from the result that the activity was not lowered even after using 4 times.

Table 5

| Enzyme | Sample | 1 | 2 | 3 | 4 |
|---|---|---|---|---|---|
| alkaline protease | 1 | 10.6% | 12.7% | 15.1% | 12.1% |
| | 2 | 10.6 | 12.1 | 13.6 | 13.0 |
| | 3 | 1.6 | 0 | 0 | — |
| neutral protease | 1 | 13.3 | 13.8 | 14.5 | 14.0 |
| | 2 | 17.3 | 16.9 | 17.1 | 18.1 |
| | 3 | 8.3 | 7.3 | 4.6 | — |
| acidic protease | 1 | 27.6 | 24.3 | 22.7 | 20.7 |
| | 2 | 37.9 | 30.7 | 34.5 | 32.5 |
| | 3 | 3.5 | 2.1 | 1.4 | — |

EXAMPLE 14

Solutions A, B, C and D were prepared respectively, and their composition is as follows:

Solution A: 50 g of acrylamide, 1.6 g bisacrylamide, 100 ml of buffer solution at pH 7.0
Solution B: 30 g of sodium acrylate, 70 ml of water
Solution C: 1% catalase solution in buffer at pH 7.0
Solution D: 10% soluble starch solution.

These solutions were mixed together in the range described in Table 6 and samples 1 and 2 were prepared.

Table 6

| Sample | Solution A | B | C | D |
|---|---|---|---|---|
| | ml | ml | ml | ml |
| 1 | 2.0 | 0 | 1.0 | 1.0 |
| 2 | 2.0 | 2.0 | 1.0 | 1.0 |

After freezing, Samples 1, and 2 were subjected to 54 Krad of irradiation. Then, phosphate buffer (pH 7.0, 1/15M), the enzyme preparation and 5% hydrogen peroxide were mixed together and was incubated at 30°C for 10 minutes.

The recover of the preparation was determined by measuring the volume of oxygen generated. The results were shown in Table 7.

Table 7

| Sample | Activity |
|---|---|
| 1 | 45.6% |
| 2 | 94.1 |

EXAMPLE 15

Solutions A, B, C and D were prepared respectively, and their composition is described below.

Solution A: 30 g of acrylamide, 1.6 g of bis-acrylamide, 100 g of water at pH 4.5

Solution B: 30% potassium acrylate solution (pH 4.5)

Solution C: 1% glucozyme (glucoamylase) solution (pH 4.5)

Solution D: 10% soluble starch.

These solutions were mixed together in the range described in Table 8 and Samples 1 and 2 were prepared.

Table 8

| Solution Sample | A | B | C | D |
|---|---|---|---|---|
| | ml | ml | ml | ml |
| 1 | 2.0 | 0 | 1.0 | 2.0 |
| 2 | 2.0 | 2.0 | 1.0 | 0 |

After freezing, Samples 1 and 2 were subjected to 75.5 Krad of irradiation with $^{60}Co$.

Enzyme activity of the water-insoluble preparation obtained was measured by the Somogy method. The results were shown in Table 9.

Table 9

| Sample | Activity |
|---|---|
| 1 | 6.7% |
| 2 | 22.1 |

EXAMPLE 16

Solutions A, B and C were prepared respectively, of which compositions were as follows:

Solution A: 50 g of acrylamide, 1.6 g of bis-acrylamide, 100 g of water (pH 8.0)

Solution B: ($B_1$) 30% sodium acrylate (pH 8.0) or ($B_2$) 30% potassium acrylate (pH 8.0)

Solution C: 2% acylase (N-acetylacylase) in Beronal buffer at pH 8.0.

Two ml of solution A was mixed with 2.0 ml of solution $B_1$ or $B_2$ and 1.0 ml of solution C. The mixture was frozen and then, was subjected to 57.1 Krad of irradiation.

The water-insoluble membraneous preparation obtained was washed. 1 g of the preparation and 2ml of $CoCl_2$ solution ($0.5 \times 10^{-3}M$) as an enzyme activator were added to 6 ml of 1/10M Beronal buffer at pH 8.0. The mixture was shaken with 2 ml of a substrate solution (1/10M, N-acetyl-D,L-methionine) at 37°C for 30 minutes.

After termination of reaction, 2 ml of the reaction mixture was boiled for 3 minutes and then, was added with 2 ml of ninhydrin solution and 0.1 ml of $SnCl_2$ solution (1/100M). The mixture was boiled for 20 minutes. After cooling, 10 ml of 50% propyl alcohol was added to the mixture.

The enzyme activity of the preparation was assayed colorimetrically at 570 m$\mu$. As a control, 1 ml of acylase solution was used.

The recovery of the activity was 45.2% in the case of solution $B_1$ and was 40.9% in the case of solution $B_2$.

Also, the activity of the enzyme preparation obtained by using solution $B_1$, i.e. sodium acrylate as a monomer was not lowered even after 6 times uses, as shown in Table 10.

Table 10

| Number of Use | Activity |
|---|---|
| 1 | 45.2% |
| 2 | 50.3 |
| 3 | 46.5 |
| 4 | 44.0 |
| 5 | 47.8 |
| 6 | 45.3 |
| average | 46.5 |

What is claimed is:

1. Process for producing a water insoluble enzyme which comprises mixing together (i) at least one water soluble monomer selected from the group consisting of acrylamide, bisacrylamide, acrylic acid, sodium acrylate, potassium acrylate and calcium acrylate, and (ii) an enzyme, freezing the resultant mixture at a temperature below about −5°C and maintaining the thus obtained frozen material at said temperature, irradiating said frozen material with a dose of from about 40 to about 100 Krad of gamma rays or X-rays under aerobic conditions to polymerize said monomer and entrap the enzyme in the resulting polymer lattice, and thereafter recovering the enzyme product.

2. Process according to claim 1, wherein said mixture solution contains in addition (iii) an organic substance which promotes the polymerization yield and protects the highly purified enzyme from radiation inactivation.

3. Process according to claim 1, wherein a step of lyophilizing the frozen material is carried out after the step of irradiation.

4. Process according to claim 1, wherein said enzyme is a member selected from the group consisting of amylase, glucoamylase, glucose isomerase, acylase, protease, D-amino acid oxidase, catalase and invertase.

5. Process for producing a water insoluble enzyme which comprises mixing together (i) at least one water soluble monomer selected from the group consisting of acrylamide, bisacrylamide, acrylic acid, sodium acrylate, potassium acrylate and calcium acrylate, each of said monomers being capable of being radiopolymerized, (ii) an enzyme, and (iii) an organic substance to promote the polymerization yield and protect the said enzyme from radiation inactivation, freezing the resultant mixture at a temperature from about −100°C to about −5°C, irradiating the resultant frozen mixture at said temperature under aerobic conditions with a dose of from about 140 to about 100 Krad of ionizing gamma radiation to polymerize said manomer and entrap the enzyme in the resulting polymer lattice, lyophilizing the resultant irradiated frozen polymer material and thereafter recovering an irradiated enzyme product which is in a sponge-like, membrane form that maintains its structure when immersed in water.

6. Process according to claim 5, wherein said enzyme is a member selected from the group consisting of amylase, glucoamylase, glucose isomerase, acylase, protease, D-amino acid oxidase, catalase and invertase.

7. Process according to claim 5, wherein said organic substance is a protein.

8. Process according to claim 5, wherein said organic substance is a starch.

9. Process according to claim 5, wherein said organic substance is a sugar.

10. Process according to claim 5, wherein said organic substance is glycerine.

\* \* \* \* \*